United States Patent [19]
Lund et al.

[11] Patent Number: 5,916,798
[45] Date of Patent: Jun. 29, 1999

[54] METHOD OF OBTAINING A CELLULOSIC TEXTILE FABRIC WITH REDUCED TENDENCY TO PILLING FORMATION

[75] Inventors: Henrik Lund, Copenhagen; Hanne Høst Pedersen, Lyngby, both of Denmark

[73] Assignee: Novo Nordisk A/S, Bagsvaerd, Denmark

[21] Appl. No.: 08/836,340

[22] PCT Filed: Dec. 5, 1995

[86] PCT No.: PCT/DK95/00488

§ 371 Date: May 8, 1997

§ 102(e) Date: May 8, 1997

[87] PCT Pub. No.: WO96/17994

PCT Pub. Date: Jun. 13, 1996

[30] Foreign Application Priority Data

Dec. 5, 1994 [DK] Denmark .................................. 1387/94

[51] Int. Cl.[6] ...................................................... C12S 11/00
[52] U.S. Cl. ................................................................ 435/263
[58] Field of Search .............................................. 435/263

[56] References Cited

FOREIGN PATENT DOCUMENTS

WO 93/13261  7/1993  WIPO .
WO 94/12578  6/1994  WIPO .

OTHER PUBLICATIONS

Bazin et al., "Enzymatic Bio–Polishing of Cellulosic Fabric", Novo Nordisk Bioindustrial Group, Enzyme Process Division, , Jan. 3, 1992, pp. 1–6.

Dialog Information Services, Textile Technology Digest, Accession No. 0550586, 06766/91, Cotton Grower: "Putting The Polish On Cotton Fabric", 27, No. 7: 20–21 (Jul. 1991).

*Primary Examiner*—Charles L. Patterson, Jr.
*Attorney, Agent, or Firm*—Steve T. Zelson, Esq.; Valeta Gregg, Esq.

[57] ABSTRACT

A method for obtaining a cellulosic textile fabric having a strongly reduced tendency to pilling formation, preferably corresponding to a pilling note of at least 4, more preferably of at least 4.5, which method comprises treating the fabric with a cellulase capable of performing a partial hydrolysis of the fibre surface corresponding to a <2% weight loss based on the untreated cellulosic textile fabric. The cellulase is preferably a 43 kD endoglucanase derived from or producible by *Humicola insolens,* DSM 1800, SEQ ID NO:1, or a functional analogue of said cellulase such as a variant which is modified by substitution of one or more amino acid residues in one or more of the positions 8, 55, 58, 62, 67, 132, 147, 162, 221, 222, 223, 280; or modified by truncation, preferably genetically truncation, at any position from position 213.

13 Claims, No Drawings

METHOD OF OBTAINING A CELLULOSIC TEXTILE FABRIC WITH REDUCED TENDENCY TO PILLING FORMATION

CROSS-REFERENCE TO RELATED APPLICATIONS

This application is a 35 U.S.C. 371 national application of PCT/DK95/00488 filed Dec. 5, 1995 and claims priority under 35 U.S.C. 119 Danish application 1387/94 filed Dec. 5, 1994, the contents of which applications are fully incorporated herein by reference.

The present invention relates to a method for obtaining a cellulosic textile fabric having a strongly reduced tendency to pilling formation. More specifically, the invention relates to a method wherein the cellulosic textile fabric is subjected to an enzymatic treatment with a cellulase without substantial weight loss.

BACKGROUND OF THE INVENTION

Without the application of finishing components, most cotton fabrics and cotton blend fabrics have a handle appearance that is rather hard and stiff. The fabric surface also is not smooth because small fuzzy microfibrils protrude from it. In addition, after a relatively short period of wear, pilling appears on the fabric surface thereby giving it an unappealing, worn look.

A known method for obtaining a soft and smooth fabric is to subject cellulosic fabrics to treatment by cellulolytic enzymes during their manufacture. This treatment is known as Bio-Polishing (hereinafter denoted biopolishing), cf. *Bazin j. and Sasserod, S.: Enzymatic Bio-Polishing of Cellulosic Fabric,* Paper presented on Oct. 25th, 1991, at "58ème Congrès de l'Association des Chimistes de l'Industrie Textile", Mulhouse, France, which is hereby incorporated by reference.

Biopolishing is a specific treatment of the yarn surface which improves fabric quality with respect to handle and appearance without loss of fabric wettability. The most important effects of biopolishing can be characterised by less fuzz and pilling, increased gloss/luster, improved fabric handle, increased durable softness and improved water absorbency.

Biopolishing usually takes place in the wet processing of the manufacture of knitted and woven fabrics. Wet processing comprises such steps as e.g. desizing, scouring, bleaching, washing, dying/printing and finishing. During each of these steps, the fabric can be subjected to mechanical action.

However, since the cellulolytic enzymes catalyse hydrolysis of the cellulosic fibre surface, the enzymatic action will eventually result in a weight loss of fibre or fabric. Even though the biopolishing is carried out in such a way so as to obtain a controlled, partial hydrolysis of the fibre surface, a proper polishing effect without excessive loss of fabric strength has hitherto been obtained at a weight loss of fabric of 3–5 w/w %. Such a weight loss is undesirable for the textile industry and, for economical reasons, makes the biopolishing process less desirable.

Thus, it is the object of the present invention to provide a method for obtaining a cellulosic textile fabric with strongly reduced tendency to pilling formation but without substantial weight loss of fabric.

SUMMARY OF THE INVENTION

Surprisingly, it has been found that it is possible to obtain a cellulosic textile fabric having a strongly reduced tendency to pilling formation at a significantly reduced weight loss by subjecting the fabric to a biopolishing process, preferably using monocomponent cellulases.

Accordingly, the method of the invention comprises treating a cellulose-fibre-containing textile fabric with a cellulase capable of performing a partial hydrolysis of the fibre surface corresponding to a weight loss of less than 2 w/w %, based on the untreated cellulosic textile fabric, or corresponding to a weight loss of less than about 2%, calculated as the difference, in terms of percentage, of the weight loss of the cellulase treated textile fabric and the weight loss of the textile fabric treated without cellulase (blank).

DETAILED DESCRIPTION OF THE INVENTION

The fabric

In the present context, the terms "cellulosic textile fabric" and "cellulose-fibre-containing textile fabric" are intended to indicate any type of fabric, in particular woven or knitted fabric, prepared from a cellulose-containing material, containing cellulose or cellulose derivatives, e.g. from wood pulp, and cotton. Also, in the present context, the term "fabric" is intended to include garments and other types of processed fabrics. Examples of cellulosic textile fabric is cotton, viscose (rayon); lyocell; flax (linen); all blends of viscose, cotton or lyocell with other fibers such as polyester; viscose/cotton blends, lyocell/cotton blends, viscose/wool blends, lyocell/wool blends, cotton/wool blends; flax (linen), ramie and other fabrics based on cellulose fibers, including all blends of cellulosic fibers with other fibers such as wool, polyamide, acrylic and polyester fibers, e.g. viscose/cotton/polyester blends, wool/cotton/polyester blends, flax/cotton blends etc.

In the present context, the term "strongly reduced tendency to pilling formation" is intended to mean a permanent (and excellent) resistance to formation of pills on the surface of the treated (biopolished) fabric surface in comparison with fabric which has not been subjected to the method of the present invention. The tendency to pilling formation may be tested according to the Swiss norm SN 198525, published in 1990 by Schweizerische Normen-Vereinigung, Kirchenweg 4, Postfach, CH-8032 Zürich, Switzerland, which describes a test of pilling-resistance for textiles which in turn is based on the Swiss norms SNV 95 150 (Textiles—Standard climatic conditions and test conditions for the physical tests under standard climate conditions) and SN 198 529 (Testing of textiles—"Scheuerfestigkeit"—Martindale method). The results of the test is expressed in terms of "pilling notes" which is a rating on a scale from pilling note 1 (heavy pill formation) to pilling note 5 (no or very little pill formation), allowing ½ pilling notes.

In a preferred embodiment of the present invention, the method provides a textile fabric preferably having a pilling note of at least 4, more preferably of at least 4.5, especially of 5, measured according to SN 198525 (1990).

In another preferred embodiment, the method of the invention provides a textile fabric having rating which is at least 1, preferably at least 2, especially at least 3, pilling note(s) higher than of the corrsponding untreated textile fabric; the absolute pilling notes being measured according to SN 198525 (1990).

According to the method of the invention, the partial hydrolysis of the fibre surface corresponds to a weight loss of less than about 2 w/w %, preferably a weight loss of less than about 1.8 w/w %, more preferably of less than about 1.5 w/w %.

The weight loss is determined under controlled conditions, i.e. according to SNV 95150, vide supra. The weight loss is expressed as the difference, in terms of percentage, of the weight loss of the cellulase treated textile fabric and the weight loss of the textile fabric treated without cellulase (blank).

The process

As mentioned above, cellulase treatment of the fabric may be carried out simultaneously with other fabric manufacturing procedures, e.g. desizing, or after the bleaching of the fabric.

It is to be understood that the method of the invention can be carried out in any conventional wet textile processing step, preferably after the desizing or bleaching of the textile fabric, either simultanously with a conventional (well-known) process step or as an additional process step. The method will typically be accomplished in high-speed circular systems such as jet-overflow dyeing machines, high-speed winches and jiggers. An example of a useful High-speed system is the "Aero 1000" manufactured by Biancalani, Italy. Alternatively, the method can be accomplished in a two-step biopolishing process, e.g. as disclosed in the International Patent Application published as WO 93/20278, wherein the first step is a separate cellulase treatment which is carried out essentially without mechanical treatment, and followed by a second step wherein the fabric is subjected to a mechanical treatment. This cellulase treatment can be carried out in a J-Box, on a Pad-Roll or in a Pad-Bath.

Cellulase treatment according to the present invention and desizing are reconcilable processes that can be conducted at the same conditions, i.e. pH, temperature, dosage/time ratio, etc. By performing these processes simultaneously, the overall fabric manufacturing process becomes shortened. Such time saving arrangements are a major benefit of the process of the invention.

Enzyme dosage greatly depends on the enzyme reaction time, i.e. a relatively short enzymatic reaction time necessitates a relatively increased enzyme dosage, and vice versa. In general, enzyme dosage may be stipulated in accordance with the reaction time available. In this way cellulase treatment of the fabric according to the present invention can be brought into conformity with e.g. the desizing conditions, if for instance these two reactions are to be carried out simultaneously.

An enzyme dosage/time ratio similar to what is known from conventional biopolishing may be used. Preferred enzyme dosages are from about 100 to about 100,000 ECU/kg fabric, more preferably from about 500 to about 20,000 ECU/kg fabric, especially from about 1000 to about 5,000 ECU/kg fabric.

Typically, the reaction time is from about 10 minutes to about 4 hours, preferably from about 20 minutes to about 2 hours but the reaction can be carried out for any period of time between about 1 minute and about 24 hours, in dependence of the specific type of processing equipment.

The method of the invention may be carried out in the presence of certain components which can be added to the cellulase, i.e. the formulated cellulase composition, or separately to the wash liquor wherein the enzyme treatment takes place. Examples of such components include a stabilizer, a wetting agent, a buffer and a dispersing agent. The stabilizer may be an agent stabilizing the cellulolytic enzyme.

The wetting agent serves to improve the wettability of the fibre whereby a rapid and even desizing may be obtained. The wetting agent is preferably of an oxidation stable type.

The buffer may suitably be a phosphate, borate, citrate, acetate, adipate, triethanolamine, monoethanolamine, diethanolamine, carbonate (especially alkali metal or alkaline earth metal, in particular sodium or potassium carbonate, or ammonium and HCl salts), diamine, especially diaminoethane, imidazole, or amino acid buffer. Preferably, the buffer is a mono-, di-, or triethanolamine buffer.

The dispersing agent may suitably be selected from nonionic, anionic, cationic, ampholytic or zwitterionic surfactants. More specifically, the dispersing agent may be selected from carboxymethylcellulose, hydroxypropylcellulose, alkyl aryl sulphonates, long-chain alcohol sulphates (primary and secondary alkyl sulphates), sulphonated olefins, sulphated monoglycerides, sulphated ethers, sulphosuccinates, sulphonated methyl ethers, alkane sulphonates, phosphate esters, alkyl isothionates, acyl sarcosides, alkyl taurides, fluorosurfactants, fatty alcohol and alkylphenol condensates, fatty acid condensates, condensates of ethylene oxide with an amine, condensates of ethylene oxide with an amide, block polymers (polyethylene glycol, polypropylene glycol, ethylene diamine condensed with ethylene or propylene oxide), sucrose esters, sorbitan esters, alkyloamides, fatty amine oxides, ethoxylated monoamines, ethoxylated diamines, ethoxylated polyamines, ethoxylated amine polymers and mixtures thereof.

Preferably, the dispersing agent is an ethoxylated fatty acid ester or a nonylphenyl polyethyleneglycol ether.

Further, the method of the invention may be carried out in the presence of a conventional antiredepostion agent, e.g. polymeric agents such as polyvinylpyrrolidone (PVP), carboxymethylcellulose (CMC), and polyacrylates.

The enzyme

In the present context, the term "cellulase" or "cellulolytic enzyme" refers to an enzyme which catalyses the degradation of cellulose to glucose, cellobiose, triose and other cellooligosaccharides.

In the present context the term "enzyme" or "cellulase enzyme" is understood to include a mature protein or a precursor form thereof as well to a functional fragment thereof which essentially has the activity of the full-length enzyme. Furthermore, the term "enzyme" is intended to include homologues or analogues of said enzyme. Such homologues comprise an amino acid sequence exhibiting a degree of identity of at least 60% with the amino acid sequence of the parent enzyme, i.e. the parent cellulase. The degree of identity may be determined by conventional methods, see for instance, Altshul et al., *Bull. Math. Bio.* 48: 603–616, 1986, and Henikoff and Henikoff, *Proc. Natl. Acad. Sci. USA* 89: 10915–10919, 1992. Briefly, two amino acid sequences are aligned to optimize the alignment scores using a gap opening penalty of 10, a gap extension penalty of 1, and the "blosum 62" scoring matrix of Henikoff and Henikoff, supra.

Alternatively, the homologue or analogue of the enzyme may be one encoded by a nucleotide sequence hybridizing with an oligonucleotide probe prepared on the basis of the nucleotide sequence or an amino acid sequence under the following conditions: presoaking in 5×SSC and prehydbridizing for 1 hr. at about 40° C. in a solution of 20% formamide, 5×Denhardt's solution, 50 mM sodium phosphate, pH 6.8, and 50 $\mu$g denatured sonicated calf thymus DNA, followed by hybridization in the same solution supplemented with 100 $\mu$M ATP for 18 hrs. at about 40° C., followed by a wash in 0.4×SSC at a temperature of about 45° C.

Molecules to which the oligonucleotide probe hybridizes under these conditions are detected using standard detection procedures (e.g. Southern blotting).

Homologues of the present enzyme may have one or more amino acid substitutions, deletions or additions. These changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glylocine, alanine, serine, threonine, methionine).

It will be apparent to persons skilled in the art that such substitutions can be made outside the regions critical to the function of the molecule and still result in an active enzyme. Amino acids essential to the activity of the enzyme of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for cellulolytic activity to identify amino acid residues that are critical to the activity of the molecule. Sites of ligand-receptor interaction can also be determined by analysis of crystal structure as determined by such techniques as nuclear magnetic resonance, crystallography or photoaffinity labelling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The homologue may be an allelic variant, i.e. an alternative form of a gene that arises through mutation, or an altered enzyme encoded by the mutated gene, but having substantially the same activity as the enzyme of the invention. Hence mutations can be silent (no change in the encoded enzyme) or may encode enzymes having altered amino acid sequence.

The homologue of the present enzyme may also be a genus or species homologue, i.e. an enzyme with a similar activity derived from another species.

A homologue of the enzyme may be isolated by preparing a genomic or cDNA library of a cell of the species in question, and screening for DNA sequences coding for all or part of the homologue by using synthetic oligonucleotide probes in accordance with standard techniques, e.g. as described by Sambrook et al., *Molecular Cloning:A Laboratory Manual,* 2nd. Ed. Cold Spring Harbor Laboratory, Cold Spring Harbor, N.Y., 1989, or by means of polymerase chain reaction (PCR) using specific primers as described by Sambrook et al., supra.

Preferably, the cellulolytic enzyme to be used in the method of the invention is a monocomponent (recombinant) cellulase, i.e. a cellulase essentially free from other proteins or cellulase proteins. A recombinant cellulase component may be cloned and expressed according to standard techniques conventional to the skilled person.

In a preferred embodiment of the invention, the cellulase to be used in the method is an endoglucanase (EC 3.2.1.4), preferably a monocomponent (recombinant) endoglucanase.

Preferably, the cellulase is a microbial cellulase, more preferably a bacterial or fungal cellulase. Examples of bacterial cellulases are cellulases derived from or producible by bacteria from the group of genera consisting of Pseudomonas or *Bacillus lautus.*

The cellulase or endoglucanase may be an acid, a neutral of an alkaline cellulase or endoglucanase, i.e. exhibiting maximum cellulolytic activity in the acid, neutral of alkaline range, respectively.

Accordingly, a useful cellulase is an acid cellulase, preferably a fungal acid cellulase, more preferably a fungal acid cellulase enzyme with substantial cellulolytic activity at acidic conditions which is derived from or producible by fungi from the group of genera consisting of Trichoderma, Actinomyces, Myrothecium, Aspergillus, and Botrytis.

A preferred useful acid cellulase is derived from or producible by fungi from the group of species consisting of *Trichoderma viride, Trichoderma reesei, Trichoderma longibrachiatum, Myrothecium verrucaria, Aspergillus niger, Aspergillus oryzae,* and *Botrytis cinerea.*

Another useful cellulase or endoglucanase is a neutral or alkaline cellulase, preferably a fungal neutral or alkaline cellulase, more preferably a fungal alkaline cellulase or endoglucanase with substantial cellulolytic activity at alkaline conditions which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium.

A preferred alkaline cellulase is derived from or producible by fungi from the group of species consisting of *Humicola insolens, Fusarium oxysporum, Myceliopthora thermophile,* or *Cephalosporium sp.,* preferably from the group of species consisting of *Humicola insolens,* DSM 1800, *Fusarium oxysporum,* DSM 2672, *Myceliopthora thermophile,* CBS 117.65, or *Cephalosporium sp.,* RYM-202.

A preferred example of a native or parent cellulase is an alkaline endoglucanase which is immunologically reactive with an antibody raised against a highly purified ~43 kD endoglucanase derived from *Humicola insolens,* DSM 1800, or which is a derivative of the ~43 kD endoglucanase exhibiting cellulase activity. A preferred endoglucanase component has the amino acid sequence enclosed as SEQ ID No. 1 which is also disclosed in the International Patent Application published as WO 91/17243, SEQ ID#2, which is hereby incorporated by reference. Another preferred endoglucanase component is the core enzyme corresponding to the amino acid sequence enclosed as SEQ ID No. 1, but having the amino acid sequence corresponding to position 1–213, i.e. truncated at position 213. It is contemplated that other useful endoglucanases are enzymes having amino acid sequences corresponding to the amino acid sequence enclosed as SEQ ID No. 1, but which are truncated, preferably genetically truncated, at any position between position 213 and position 247 of the SEQ ID No. 1, i.e. having an amino acid sequence consisting of between 213 and 247 amino acid residues.

Other examples of useful cellulases are variants having, as a parent cellulase, a cellulase of fungal origin, e.g. a cellulase derivable from a strain of the fungal genus Humicola, Trichoderma or Fusarium. For instance, the parent cellulase may be derivable from a strain of the fungal species *H. insolens, Trichoderma reesei* or *F. oxysporum,* preferably the ~43 kD endoglucanase derived from *Humicola insolens,* DSM 1800, or is a functional analogue of any of said parent cellulases which i) comprises an amino acid sequence being at least 60% homologous with the amino acid sequence of the parent cellulase, ii) reacts with an antibody raised against the parent cellulase, and/or iii) is encoded by a DNA sequence which hybridizes with the same probe as a DNA sequence encoding the parent cellulase.

Property i) of the analogue is intended to indicate the degree of identity between the analogue and the parent cellulase indicating a derivation of the first sequence from the second. In particular, a polypeptide is considered to be homologous to the parent cellulase if a comparison of the respective amino acid sequences reveals an identity of greater than about 60%, such as above 70%, 80%, 85%, 90% or even 95%. Sequence comparisons can be performed via known algorithms, such as the one described by Lipman and Pearson (1985).

The additional properties ii) and iii) of the analogue of the parent cellulase may be determined as follows:

Property ii), i.e. the immunological cross reactivity, may be assayed using an antibody raised against or reactive with at least one epitope of the parent cellulase. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989.

The oligonucleotide probe used in the characterization of the analogue in accordance with property iii) defined above, may suitably be prepared on the basis of the full or partial nucleotide or amino acid sequence of the parent cellulase. The hybridization may be carried out under any suitable conditions allowing the DNA sequences to hybridize. For instance, such conditions are hybridization under specified conditions, e.g. involving presoaking in 5×SSC and prehybridizing for 1h at ~40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18h at ~40° C., or other methods described by e.g. Sambrook et al., 1989.

Examples of useful cellulase variants are variants of the 43 kD endoglucanase derived from or producible by *Humicola insolens,* DSM 1800, SEQ ID NO:1, modified by substitution of one or more amino acid residues in one or more of the positions 8, 55, 58, 62, 67, 132, 147, 162, 221, 222, 223, 280; and optionally further modified by truncation, preferably genetically truncation, at any position from position 213.

Preferred cellulase variants are variants of the 43 kD endoglucanase derived from or producible by *Humicola insolens,* DSM 1800, SEQ ID NO:1, modified by substitution of one or more amino acid residues as follows:
Y8F
S55E/D
D58A/S/N
W62E
D67R/N
F132A/D/E/G
Y147S
A162P
V221S
N222S
Q223T
Y280F.

Surprisingly, it has been found that, in case of using an alkaline endoglucanase such as the 43 kD *H. insolens,* DSM 1800, endoglucanase or the mentioned modified variants thereof, it may be advantageous to carry out the method of the present invention at a pH below about 9, preferably at a pH below 6, more preferably at a pH of from about 4.5 to about 5.5, especially at a pH of about 5.0.

In the context of this invention, cellulase activity can be expressed in ECU. Cellulolytic enzymes hydrolyse CMC, thereby increasing the viscosity of the incubation mixture. The resulting reduction in viscosity may be determined by a vibration viscosimeter (e.g. MIVI 3000 from Sofraser, France).

Determination of the cellulolytic activity, measured in terms of ECU, may be determined according to the following analysis method (assay): The ECU assay quantifies the amount of catalytic activity present in the sample by measuring the ability of the sample to reduce the viscosity of a solution of carboxy-methylcellulose (CMC). The assay is carried out at 40° C.; pH 7.5; 0.1M phosphate buffer; time 30 min; using a relative enzyme standard for reducing the viscosity of the CMC(carboxymethylcellulose Hercules 7 LFD) substrate; enzyme concentration approx. 0.15 ECU/ml. The arch standard is defined to 8200 ECU/g.

Although the useful cellulase may be used as such in the method of the present invention, it is preferred that it is formulated into a suitable composition. Thus, the useful cellulase may be used in the form of a granulate, preferably a non-dusting granulate, a liquid, in particular a stabilized liquid, a slurry, or in a protected form. Dust free granulates may be produced, e.g. as disclosed in U.S. Pat. No. 4,106,991 and U.S. Pat. No. 4,661,452 (both to Novo Nordisk A/S) and may optionally be coated by methods known in the art.

Liquid enzyme preparations may, for instance, be stabilized by adding a polyol such as e.g. propylene glycol, a sugar or sugar alcohol or acetic acid, according to established methods. Other enzyme stabilizers are well known in the art. Protected enzymes may be prepared according to the method disclosed in EP 238 216.

The performance of enzymes greatly depends on process conditions such as e.g. pH and temperature. In accomplishing the process of this invention, of course, factors such as e.g. pH-dependent performance and thermal stability should be taken into consideration in the choice of cellulytic enzymes. Other conditions such as e.g. the addition of wetting agents, etc., also depend on the overall process to be performed, as well as the enzyme employed.

The invention is further illustrated by the following non-limiting example.

EXAMPLE

Apparatus:
The test was carried out in an Atlas LP2 Launder-O-Meter using 2 swatches per beaker.
Textile:
Bleached interlock knitted 100% cotton fabric, 205 g/m².
The fabric was cut into pieces of a size 14×12 cm (about 3.5 g each) and conditioned overnight at 20° C. and 65% relative humidity under constant conditions.
Enzymes:
A: Reference (Cellusoft L, a commercial acid cellulase preparation produced and sold by Novo Nordisk A/S, DK-2880 Bagsvaerd, Denmark).
B: 43 kD endoglucanase from *Humicola insolens,* DSM 1800.
C: Variant of B (substitution D58A)
D: Variant of B (substitution F132D)
E: Variant of B (substitution Y280F)
F: Variant of B (substitution D67R)

G: Variant of B (substitution Y147S)
H: Variant of B (substitution S55E)
J: Variant of B (substitutions Y8F, W62E, A162P, V221S, N222S, Q223T)
K: Variant of B (substitution Y147N)

Experimental conditions:
(Launder-O-Meter biopolishing)
4 beakers (8 swatches) were used for each test.

| | |
|---|---|
| Liquor ratio | 1:20 |
| Liquor volume | 140 ml |
| Abrasive agent | 20 steel balls (d = 14 mm, 11 g) |
| pH | 5.0 |
| Buffer | 1 g/l acetate |
| Time | 60 min |
| Temperature | 55° C. |

Inactivation:
Each test was terminated by washing all the swatches at 70° C. followed by rinsing three times in a standard European home laundry machine, AEG Öko-Lavamat 665.

Drying:
The swatches were air dried and conditioned overnight at 20° C. and 65% relative humidity.

Tests:
The commercial enzyme preparation A was tested in 4 dosages in the range 0–4.0 w/w %, based on the weight of the textile.

Each of the enzyme preparations B-K were tested in 4 dosages in the range 0–5.0 ECU/g textile.

Results:
The following parameters were measured/calculated:

* Weight loss, in terms of percentage, of the weight loss of the cellulase treated textile fabric and the weight loss of the textile fabric treated without cellulase (blank).
* Pilling note (PN), measured according to SN 198525 (1990) using a Martindale Pilling Tester at 500 revolutions.

The pilling note of the untreated textile as well as of the textile treated without cellulase (blank) was 1.

The following table shows the measured weight loss corresponding to a resulting pilling note of 4.5 of the cellulase treated textile.

TABLE

| Enzyme | Weight loss (Δ%) |
|---|---|
| A (ref.) | 5.6 |
| B | 2.0 |
| C | 1.3 |
| D | 1.3 |
| E | 2.0 |
| F | 1.7 |
| G | 1.2 |
| H | 1.0 |
| J | 1.2 |
| K | 1.5 |

We claim:

1. A method for obtaining a cellulosic textile fabric having a strongly reduced tendency to pilling formation, the method comprising treating a cellulose-fiber-containing textile fabric with a cellulase capable of performing a partial hydrolysis of the fiber surface corresponding to a weight loss of less than 2 w/w % based on the untreated cellulosic textile fabric, wherein the cellulase comprises a variant of a 43 kD endoglucanase derived from *Humicola insolens*, DSM 1800, said variant being modified by:

(a) substitution of one or more amino acid residues at one or more of the positions 8, 55, 58, 62, 67, 132, 147, 162, 221, 222, and 223 of SEQ ID NO:1; or (b) truncation between position 213 to position 247.

2. The method according to claim 1, wherein the pilling formation corresponds to a pilling note of at least 4.

3. The method according to claim 1, wherein the textile fabric contains cellulose fibers selected from the group consisting of cotton, viscose, lyocell, all blends of viscose, cotton or lyocell with other fibers such as polyester, viscose/cotton blends, lyocell/cotton blends, viscose/wool blends, lyocell/wool blends, cotton/wool blends, flax, ramie and other fabrics based on cellulose fibers, including all blends of cellulosic fibers with other fibers such as wool, polyamide, acrylic and polyester fibers.

4. A method according to claim 1, wherein the cellulase is a monocomponent cellulase.

5. The method according to claim 1, wherein the treatment is carried out at a pH below about 9.

6. The method according to claim 1, wherein said substitutions are selected from the group consisting of Y8F, S55E/D, D58A/S/N, W62E, D67R/N, F132A/D/E/G, Y147S, A162P, V221S, N222S, and Q223T.

7. The method according to claim 1, wherein the treatment is carried out in any wet processing stage of a conventional textile fabric manufacturing process.

8. The method according to claim 7, wherein the treatment is accomplished in high-speed circular systems.

9. The method according to claim 7, wherein the treatment is accomplished in a J-Box, on a Pad-Roll or in a Pad-Bath during a two-step biopolishing process.

10. The method of claim 2, wherein the pilling note is at least 4.5.

11. The method of claim 5, wherein the pH is below 6.

12. The method of claim 11, wherein the pH is about 4.5 to about 5.5.

13. The method of claim 12, wherein the pH is about 5.0.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 305 amino acids
       (B) TYPE: amino acid
       (D) TOPOLOGY: linear (ii) MOLECULE TYPE: protein (vi) ORIGINAL SOURCE:
       (A) ORGANISM: Humicola insolens
       (B) STRAIN: DSM 1800

(xi) SEQUENCE DESCRIPTION: SEQ ID NO:1:

```
Met Arg Ser Ser Pro Leu Leu Pro Ser Ala Val Val Ala Ala Leu Pro
-21 -20              -15                 -10

Val Leu Ala Leu Ala Ala Asp Gly Arg Ser Thr Arg Tyr Trp Asp Cys
 -5              1                   5                  10

Cys Lys Pro Ser Cys Gly Trp Ala Lys Lys Ala Pro Val Asn Gln Pro
             15                  20                 25

Val Phe Ser Cys Asn Ala Asn Phe Gln Arg Ile Thr Asp Phe Asp Ala
             30                  35                 40

Lys Ser Gly Cys Glu Pro Gly Gly Val Ala Tyr Ser Cys Ala Asp Gln
             45                  50                 55

Thr Pro Trp Ala Val Asn Asp Asp Phe Ala Leu Gly Phe Ala Ala Thr
 60                  65                  70                 75

Ser Ile Ala Gly Ser Asn Glu Ala Gly Trp Cys Cys Ala Cys Tyr Glu
                 80                  85                 90
```

-continued

```
Leu Thr Phe Thr Ser Gly Pro Val Ala Gly Lys Lys Met Val Val Gln
            95              100             105

Ser Thr Ser Thr Gly Gly Asp Leu Gly Ser Asn His Phe Asp Leu Asn
            110             115             120

Ile Pro Gly Gly Gly Val Gly Ile Phe Asp Gly Cys Thr Pro Gln Phe
    125             130             135

Gly Gly Leu Pro Gly Gln Arg Tyr Gly Gly Ile Ser Ser Arg Asn Glu
140             145             150                     155

Cys Asp Arg Phe Pro Asp Ala Leu Lys Pro Gly Cys Tyr Trp Arg Phe
            160             165             170

Asp Trp Phe Lys Asn Ala Asp Asn Pro Ser Phe Ser Phe Arg Gln Val
            175             180             185

Gln Cys Pro Ala Glu Leu Val Ala Arg Thr Gly Cys Arg Arg Asn Asp
        190             195             200

Asp Gly Asn Phe Pro Ala Val Gln Ile Pro Ser Ser Ser Thr Ser Ser
        205             210             215

Pro Val Asn Gln Pro Thr Ser Thr Ser Thr Thr Ser Thr Ser Thr Thr
220             225             230             235

Ser Ser Pro Pro Val Gln Pro Thr Thr Pro Ser Gly Cys Thr Ala Glu
            240             245             250

Arg Trp Ala Gln Cys Gly Gly Asn Gly Trp Ser Gly Cys Thr Thr Cys
            255             260             265

Val Ala Gly Ser Thr Cys Thr Lys Ile Asn Asp Trp Tyr His Gln Cys
            270             275             280

Leu
```